United States Patent
Cochran et al.

(10) Patent No.: US 9,417,145 B2
(45) Date of Patent: Aug. 16, 2016

(54) CAP ANALYSIS TECHNIQUE

(71) Applicants: Don W. Cochran, Gates Mills, OH (US); Thomas P. O'Brien, Chagrin Falls, OH (US); Thomas Henry Palombo, Cuyahoga Falls, OH (US); John A. Seifert, Lakewood, OH (US)

(72) Inventors: Don W. Cochran, Gates Mills, OH (US); Thomas P. O'Brien, Chagrin Falls, OH (US); Thomas Henry Palombo, Cuyahoga Falls, OH (US); John A. Seifert, Lakewood, OH (US)

(73) Assignee: Pressco Technology Inc., Cleveland, OH (US)

(*) Notice: Subject to any disclaimer, the term of this patent is extended or adjusted under 35 U.S.C. 154(b) by 0 days.

(21) Appl. No.: 14/259,051

(22) Filed: Apr. 22, 2014

(65) Prior Publication Data
US 2014/0311256 A1    Oct. 23, 2014

Related U.S. Application Data

(60) Provisional application No. 61/814,658, filed on Apr. 22, 2013.

(51) Int. Cl.
| | | |
|---|---|---|
| *G01L 3/00* | (2006.01) | |
| *G01L 5/24* | (2006.01) | |
| *B67B 3/26* | (2006.01) | |
| *G01N 21/90* | (2006.01) | |

(52) U.S. Cl.
CPC . *G01L 5/24* (2013.01); *B67B 3/261* (2013.01); *G01N 21/909* (2013.01); *G01N 21/9054* (2013.01)

(58) Field of Classification Search
CPC ........ G01L 3/00; G01L 5/24; G01N 21/9054; B67B 3/261

USPC .......... 356/240.01; 73/800, 862.08, 862.324, 73/240.01
See application file for complete search history.

(56) References Cited

U.S. PATENT DOCUMENTS

| | | | |
|---|---|---|---|
| 4,521,807 A * | 6/1985 | Werson ......................... 348/134 |
| 4,668,983 A | 5/1987 | Werson | |
| 4,682,220 A * | 7/1987 | Beurskens ......... G01N 21/9054 250/223 B |
| 4,746,212 A | 5/1988 | Sudo et al. | |
| 5,172,005 A | 12/1992 | Cochran et al. | |
| 5,321,506 A | 6/1994 | Sargent | |
| 5,365,084 A | 11/1994 | Cochran et al. | |
| 5,699,152 A | 12/1997 | Fedor et al. | |
| 6,384,421 B1 * | 5/2002 | Gochar, Jr. ............... 250/559.46 |
| 6,424,599 B1 * | 7/2002 | Ditzig ............................. 368/10 |
| 6,473,169 B1 | 10/2002 | Dawley et al. | |
| 6,643,009 B2 | 11/2003 | Takakusaki et al. | |
| 8,001,748 B2 | 8/2011 | Schulz et al. | |
| 8,388,905 B2 * | 3/2013 | Neel et al. ..................... 422/401 |
| 2002/0196434 A1 * | 12/2002 | Takakusaki et al. ........ 356/240.1 |
| 2005/0180884 A1 * | 8/2005 | Itoh ................................. 422/63 |
| 2014/0311256 A1 * | 10/2014 | Cochran et al. ............. 73/862.08 |

OTHER PUBLICATIONS

International Search Report for PCT/US2014/035047 dated Aug. 29, 2014.

* cited by examiner

*Primary Examiner* — Max Noori
(74) *Attorney, Agent, or Firm* — Fay Sharpe LLP

(57) ABSTRACT

A technique to assess or analyze cap removal or opening torque or rotational position is provided. In at least one form, a high speed, on-line machine vision system measures or determines the rotational position of a cap on a bottle, measures or determines the rotational position of the finish or neck of the same bottle, and then optionally uses such positional information to predict the opening or removal torque that will be required for a consumer to remove the bottle cap from the bottle.

42 Claims, 8 Drawing Sheets

CAP ANALYSIS TECHNIQUE

This application claims the benefit of and priority to U.S. Provisional Application No. 61/814,658, filed Apr. 22, 2013—which application is incorporated herein by reference in its entirety.

BACKGROUND

The present exemplary embodiments relate to cap analysis using imaging techniques. It finds particular application in conjunction with capping and filling stations of a container processing system, and will be described with particular reference thereto. However, it is to be appreciated that the present exemplary embodiments are also amenable to other like applications.

By way of background, a major problem for beverage suppliers is the undesired phenomenon of having container caps disposed on containers such that the consumer has difficulty removing them. There are constant complaints about this difficulty, and with an aging population (e.g. Baby Boom generation), it is anticipated that this problem with containers could become an even bigger problem.

Also, problems exist in situations where the cap is not turned onto the bottle sufficiently or properly. In these cases, for example, the cap may not be sealed properly, among other possibilities, and could have leakage problems.

BRIEF DESCRIPTION

In one aspect of the presently described embodiments, a method comprises capturing a first image of a cap fitted to a container, capturing a second image of at least a portion of a support ring of the container, wherein the capturing of the first image and the second image occurs non-simultaneously, and, analyzing the first image and the second image to determine a removal torque required to remove the cap from the container or a rotational position of the cap based on the fiducials, marks or orientation patterns.

In another aspect of the presently described embodiments, the method further comprises determining whether the removal torque or rotational position is acceptable, if the removal torque or rotational position is not acceptable, performing at least one of sending a reject signal to reject the container and sending a feedback control signal to the capping system, and, repeating the capturing, analyzing, determining and performing for subsequent caps fitted to containers.

In another aspect of the presently described embodiments, the obtaining the at least one image is accomplished using multiple cameras.

In another aspect of the presently described embodiments, the obtaining the at least one image is accomplished using telecentric lensing.

In another aspect of the presently described embodiments, the support ring is inspected using the telecentric lens.

In another aspect of the presently described embodiments, the analyzing of the at least one image comprises comparing a final rotational position of the cap relative to the container to estimate the removal torque.

In another aspect of the presently described embodiments, the rotational position is determined based on positions of fiducials or marks.

In another aspect of the presently described embodiments, the feedback control signal facilitates torque correction for multiple capper heads of the capping machine.

In another aspect of the presently described embodiments, the method further comprises using at least one of engineered lighting and filters to obtain images.

In another aspect of the presently described embodiments, a method comprises capturing a first image of a cap fitted to a container using a first camera, capturing a second image of at least a portion of a support ring of the container using a second camera, and, analyzing the first image and the second image to determine a removal torque required to remove the cap from the container or a rotational position of the cap based on the fiducials, marks or orientation patterns.

In another aspect of the presently described embodiments, a method further comprises determining whether the removal torque or rotational position is acceptable, if the removal torque or rotational position is not acceptable, performing at least one of sending a reject signal to reject the container and sending a feedback control signal to the capping system, and, repeating the capturing, analyzing, determining and performing for subsequent caps fitted to containers.

In another aspect of the presently described embodiments, the obtaining the first and second image is accomplished using telecentric lensing.

In another aspect of the presently described embodiments, the support ring is inspected using the telecentric lens.

In another aspect of the presently described embodiments, the analyzing of the at least one image comprises comparing a final rotational position of the cap relative to the container to estimate the removal torque.

In another aspect of the presently described embodiments, the rotational position is determined based on positions of fiducials or marks.

In another aspect of the presently described embodiments, the feedback control signal facilitates torque correction for multiple capper heads of the capping machine.

In another aspect of the presently described embodiments, the method further comprises using at least one of engineered lighting and filters to obtain images.

In another aspect of the presently described embodiments, a system comprises an imaging system including at least one camera and a lensing system, the imaging system being configured to capture a first image of a cap fitted to a container, capture a second image of at least a portion of a support ring of the container, wherein the capturing of the first image and the second image occurs non-simultaneously, and, a processing system configured to analyze the first image and the second image to determine a removal torque required to remove the cap from the container or a rotational position of the cap based on the fiducials, marks or orientation patterns.

In another aspect of the presently described embodiments, the processing system is configured to determine whether the removal torque or rotational position is acceptable, perform at least one of sending a reject signal to reject the container and sending a feedback control signal to the capping system if the removal torque or rotational position is not acceptable, and repeat analyzing, determining and performing for subsequent caps fitted to containers.

In another aspect of the presently described embodiments, the obtaining the at least one image is accomplished using multiple cameras.

In another aspect of the presently described embodiments, the lensing system comprises a telecentric lens system.

In another aspect of the presently described embodiments, the processing system is configured to analyze the at least one image by comparing a final rotational position of the cap relative to the container to estimate the removal torque.

In another aspect of the presently described embodiments, the rotational position is determined based on positions of fiducials or marks.

In another aspect of the presently described embodiments, the feedback control signal facilitates torque correction for multiple capper heads of the capping machine.

In another aspect of the presently described embodiments, the system further comprises a user interface.

In another aspect of the presently described embodiments, a system comprises an imaging system including at least a first camera, a second camera and a lensing system, the imaging system being configured to capture a first image of a cap fitted to a container by the first camera, capture a second image of at least a portion of a support ring of the container by a second camera, and, a processing system configured to analyze the first image and the second image to determine a removal torque required to remove the cap from the container or a rotational position of the cap based on the fiducials, marks or orientation patterns.

In another aspect of the presently described embodiments, the processing system is configured to determine whether the removal torque or rotational position is acceptable, perform at least one of sending a reject signal to reject the container and sending a feedback control signal to the capping system if the removal torque or rotational position is not acceptable, and repeat analyzing, determining and performing for subsequent caps fitted to containers.

In another aspect of the presently described embodiments, the lensing system comprises a telecentric lens system.

In another aspect of the presently described embodiments, the processing system is configured to analyze the at least one image by comparing a final rotational position of the cap relative to the container to estimate the removal torque.

In another aspect of the presently described embodiments, the rotational position is determined based on positions of fiducials or marks.

In another aspect of the presently described embodiments, the feedback control signal facilitates correction for multiple capper heads of the capping machine.

In another aspect of the presently described embodiments, the system further comprises a user interface.

DETAILED DESCRIPTION

The presently described embodiments relate to a technique to assess or analyze cap (or closure) opening, or removal, torque required for containers having caps (or closures) fitted thereon, or a rotational position of the cap on the bottle. In at least one form, the presently described embodiments relate to a high speed, on-line machine vision system which measures or determines the rotational position of the cap on a bottle, measures or determines the rotational position of the finish or neck portion (e.g. threaded, in most cases) of the same bottle, and then, in some cases, uses such positional information to predict or estimate the torque (e.g. opening or removal torque) that it will take for a consumer to remove the bottle cap from the bottle.

It should also be appreciated that, for example, conditions of 1) the cap being too difficult for the consumer to open the container, and 2) the cap not rotated or turned sufficiently onto the bottle to seal properly, may both be addressed by the presently described embodiments. Also, the rotational position of the cap may be assessed for acceptability or otherwise using the techniques of the presently described embodiments.

Figure 1:
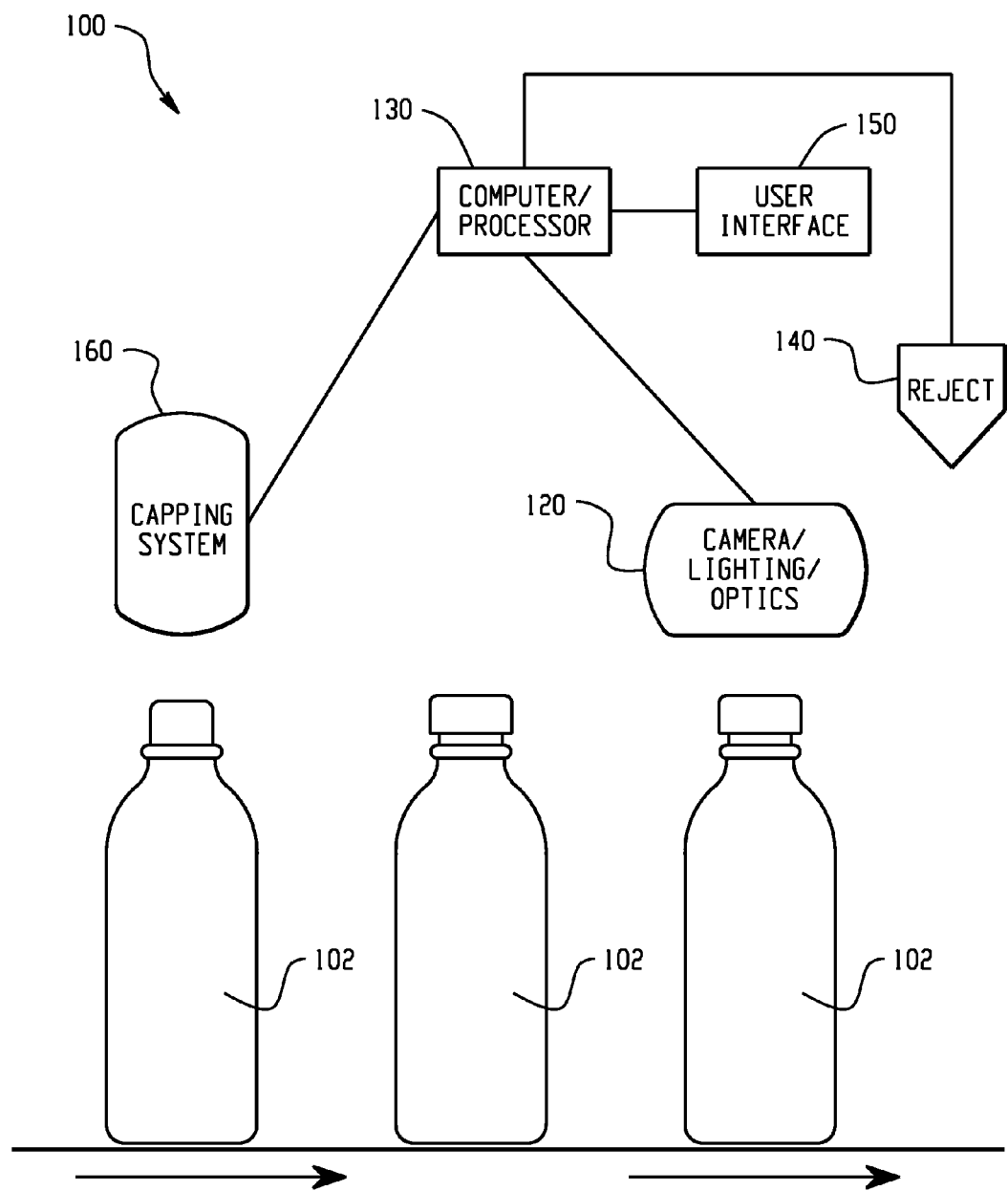
FIG. 1 is an illustration of a system according to the presently described embodiments.

There are multiple ways of executing the presently described embodiments. With reference now to FIG. 1, one example embodiment is incorporated in a capping and filling system 100 that is configured to process liquid containers, or bottles, 102. For ease of explanation, the system 100 is shown only representatively. Those of skill in the art will recognize that systems 100 may take a variety of forms to which the presently described embodiments may be applied.

As shown, each example bottle or container 102 has a neck or finish portion and support (or neck) ring. During the process, the system 100 fits a cap or closure to the bottles or containers 102. The system uses a camera/lighting/optics or imaging system 120 that may take a variety of forms (as will be described in greater detail below in example embodiments), but, in one form, views a capped bottle 102 from the top and images both the cap and also the neck or support ring (just below the cap). Multiple views and/or multiple cameras could be used. The system, which can include a variety of features including many of the features described below, obtains an image or images using one or more cameras.

In this example, after an image is obtained, the image is sent to a vision processing computer or processing element 130 (although the processor could be incorporated in the camera electronics) where the image is interrogated by way of software algorithms appropriate for the task. Such software routines may be maintained and/or executed using suitable hardware such as memory devices and/or the noted processing computers or processors in or associated with the system. However, it should be appreciated that the presently described embodiments may be implemented using a variety of hardware configurations and/or software techniques.

In at least one form, every bottle 102 is analyzed, and a determination optionally made as to whether or not the bottle 102 is within tolerance settings for the estimated removal torque or the rotational position of the cap, or, optionally, whether it is trending such that it will soon be out of tolerance. Bottles that have removal torques or rotational positions that fall outside an acceptable tolerance, e.g. based on the operators' set-up criteria, could be rejected from the line by way of a reject mechanism 140. This information may also be communicated in a number of ways, including through a user interface 150 having a user interface screen, by way of indicator lights, or communicated digitally to other computers, controllers, or displays within or beyond the immediate area, e.g. the processing plant in which the system is located—so it can be used to establish awareness of the condition of the production filling process.

The information determined in the presently described embodiments could ultimately be used to "close the loop," or be fed back, to a capping machine 160, which actually applies the torque to install the cap. Conventional capping machines typically have multiple heads and each head must typically be manually adjusted to the correct application torque and checked periodically. One of the problems is that they must be readjusted when going from large bottles (and large caps) to small ones so they have the correct torque. Also, since they typically are friction devices, when running the cappers at slower speeds, they require a different adjustment than for higher speeds because of the difference in inertia.

The presently described embodiments may also include an inspection concept that can feed back the positional or rotational information to facilitate correction optimization of individual capper head torque adjustments. That information could be used for either manual corrections or fully closed-loop modulation of the individual capper heads.

According to the presently described embodiments, the applied torque or other parameters are corrected accordingly for each of the capper heads by correlating the data to each of the capper heads, for example. In this regard, the capping machine 160 is only representatively shown. However, according to the presently described embodiments, the adjustments to the capper heads could, for example, be servo-ed, in which case the output of the inspection system could be used to close the loop. The industry has not had an on-line way of dynamically measuring the torque so servo-ed heads have not met with much acceptance to date.

Figure 2A:
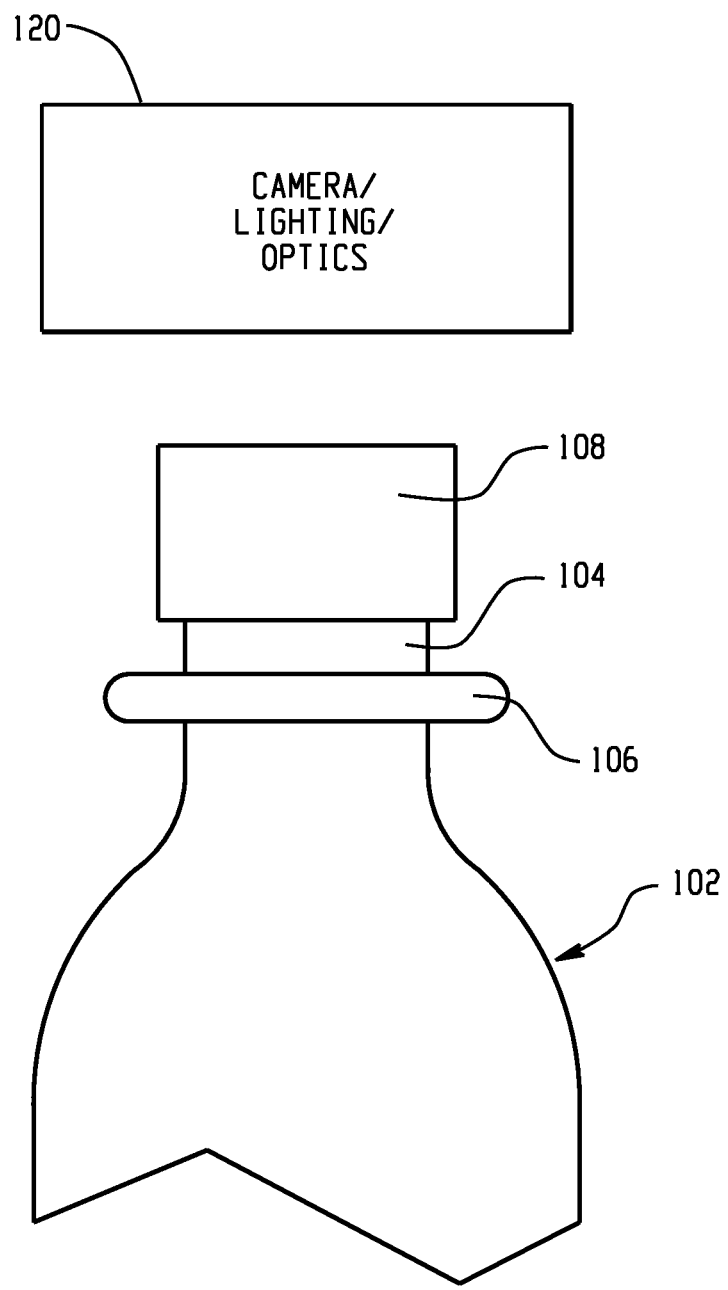
FIGS. 2(a)-2(c) are illustrations of various exemplary embodiments of a portion of the system of FIG. 1.
Figure 2B:
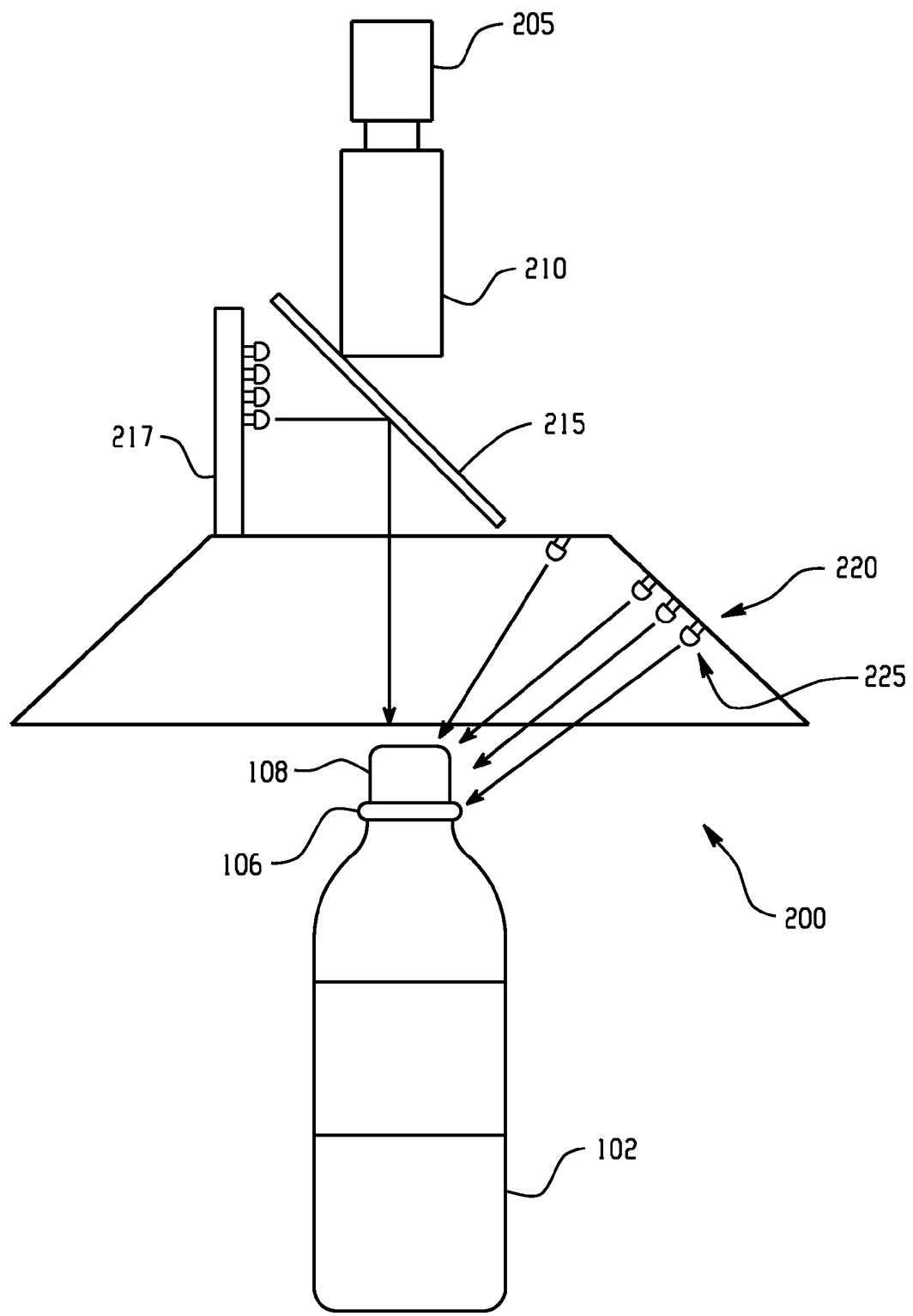

With respect to the presently described embodiments as thus far described, it should be appreciated, for example, that there is a substantial correlation between the exact rotational position of the cap, after cap application, and the rotational position of, for example, the bottle threads from the perspective of cap removal torque requirements. The rotational position of the cap alone, e.g. relative to the bottle, may also provide useful information. Refer, for example, to FIG. 2(*a*). By comparison of the final rotational position of the bottle finish or neck 104 including the neck or support ring 106 with the final applied rotation of the cap 108, an estimation of the torque that will be required to open the bottle 102 or a rotational position of the cap can be derived. In this regard, the finish area 104 of the bottle 102 and the threads molded into the cap both have tolerance limits/ranges. The estimation of the opening torque will be within its own composite tolerance range. Also, it should be appreciated that, in at least one form, the caps and support rings have fiducials, marks or orientation patterns consistently oriented with respect to a start of the respective thread elements of the cap and bottle or neck portion.

In this example, the bottle 102 is shown positioned under the imaging or camera/lighting/optics system 120. A lensing or optics system is typically incorporated within or associated with the imaging system 120, and may take a variety of forms.

In this regard, in one form, the presently described embodiments may use a telecentric lensing system, with a field of view which accounts for the positioned variations inherent in the process, allows for a high level of consistency and, therefore, provides robustness to the imaging system so the algorithms can perform more effectively. A telecentric lens system provides parallel views of the support ring, which, in one form, allows an uncompromised view of the support ring as the container moves in the field of view. A standard lens or unwrapping optics would require the container to be centered precisely from part-to-part but a telecentric lens system does not require precise centering. The telecentric system also eliminates perspective errors and provides constant magnification. All features in the field of view will remain the same size. No magnification changes occur due to cap feature and support ring feature displacement. Measurement is performed at different depths. The telecentric system maintains consistent magnification with height changes due to normal part-to-part variation. Also, optimized depth of field is provided by the telecentric system—both cap and ring features remain in focus.

The presently described embodiments may also use a technique of combining concepts of a look-in concentric lensing system, or paracentric system, with telecentric (parallel rays) lensing systems. This has the advantages of accommodating some amount of non-orthogonality of the bottle's central axis.

With reference now to FIG. 2(*b*), a system 200 incorporating a single camera is shown. In the system 200, a camera 205 is provided with a telecentric lens 210. Of course, the camera 205 may take a variety of forms. For example, the camera(s) used may be monochromatic or color cameras—each of which has advantageous features. For example, if a color camera is used, different color planes could be used to generate separate images, respectively (e.g. cap image in one color plane and a neck or support ring image in another color plane). It should be appreciated that, in at least one form, the image capturing (e.g. capturing a cap image and a support or neck ring image) may be accomplished by the camera non-simultaneously (e.g. sequentially). Likewise, although a telecentric lens is illustrated, other types of lens systems may be incorporated in the system. An optional beam splitter 215 may be provided between the lens 210 and a light source 220 (for example, having light emitting elements 225, e.g. Light Emitting Diodes LEDs, configured in suitable arrays to direct light to surfaces of interest such as the top surface of the cap 108 and the support ring 106 of the container 102). If optional beam splitter 215 is used, a lighting array 217 may be provided to generate additional axial lighting or collimated lighting.

The light source may take a variety of forms. However, using engineered lighting systems during imaging can result in much better balance of lighting or contrast between the cap and the neck ring. One example of such an engineered system is known as Chromapulse and is at least partly described in U.S. Pat. No. 5,365,084, incorporated herein by reference in its entirety. Such a system provides 1) improved light angle, e.g. front surface reflection off the neck ring, 2) minimizes contrast from water drops under the support ring, and 3) minimizes contrast on anti-rotation marks, other marks on the underside of the support ring and liquid moving behind the support ring. Such an engineered lighting system can also improve color and intensity of the imaging process, and allow for engineered sequences of lighting (e.g. pulses) to improve performance.

In one form, with continuing reference to FIG. 2(*b*), the imaging system 120 (of FIG. 1) includes at least the camera 205 and a lensing system 210. The imaging system is, in one form, configured to capture a first image of a cap fitted to a container, capture a second image of at least a portion of a support ring of the container, wherein, in at least one form, the capturing of the first image and the second image occurs non-simultaneously. Also, in one form, the processing or computer system 130 (of FIG. 1) is configured to analyze the first image and the second image to determine a removal torque required to remove the cap from the container or a rotational position of the cap. The processor or computer 130 may also determine whether the removal torque or rotational position is acceptable, perform at least one of sending a reject signal to reject the container and sending a feedback control signal to the capping system, e.g. to adjust torque applied by the capping machine, if the removal torque or rotational position is not acceptable, and repeat analyzing, determining and performing for subsequent caps fitted to containers.

With reference now to FIG. 2(*c*), a system 250 showing multiple cameras is illustrated. In the system 250, a support ring camera 255 is provided with a telecentric lens 270. Of course, as above, the camera 255 (e.g. and camera 260) may take a variety of forms. Likewise, although a telecentric lens is illustrated, other types of lens systems may be incorporated in the system. A beam splitter 265 is optional but, in one form, is disposed between the support ring camera 255 and the lens 270. Also shown is a cap camera 260 positioned to make use of the beam splitter 265 and telecentric lens 270 as well. An optional beam splitter 275 may be provided between the lens 270 and a light source 280 (for example, having light emitting elements 285, e.g. Light Emitting Diodes LEDs, configured in suitable arrays to direct light to surfaces of interest such as the top surface of the cap 108 and the support ring 106 of the container 102). If the optional beam splitter 275 is used, a lighting array 277 may be provided to generate additional axial lighting or collimated lighting.

Also shown are filters 290(a) and 290(b) disposed between the cameras and the beam splitter 265. These filters are optional. In one form, the filters are used to allow for a single flash of the illumination system or light source to obtain two different images. In this regard, the filters provide for one type of illumination for a first image (e.g. using a first camera) and a second type of illumination for a second image (e.g. using a second camera).

Like the light source 220, the light source 280 may take a variety of forms. However, as above, using engineered lighting systems during imaging can result in much better balance of lighting or contrast between the cap and the neck ring. One example of such an engineered system is known as Chromapulse and is at least partly described in U.S. Pat. No. 5,365,084, incorporated herein by reference in its entirety. Such a system provides 1) improved light angle, e.g. front surface reflection off the neck ring, 2) minimizes contrast from water drops under the support ring, and 3) minimizes contrast on anti-rotation marks, other marks on the underside of the support ring and liquid moving behind the support ring. Such an engineered lighting system can also improve color and intensity of the imaging process, and allow for engineered sequences of lighting (e.g. pulses) to improve performance.

Figure 2C:
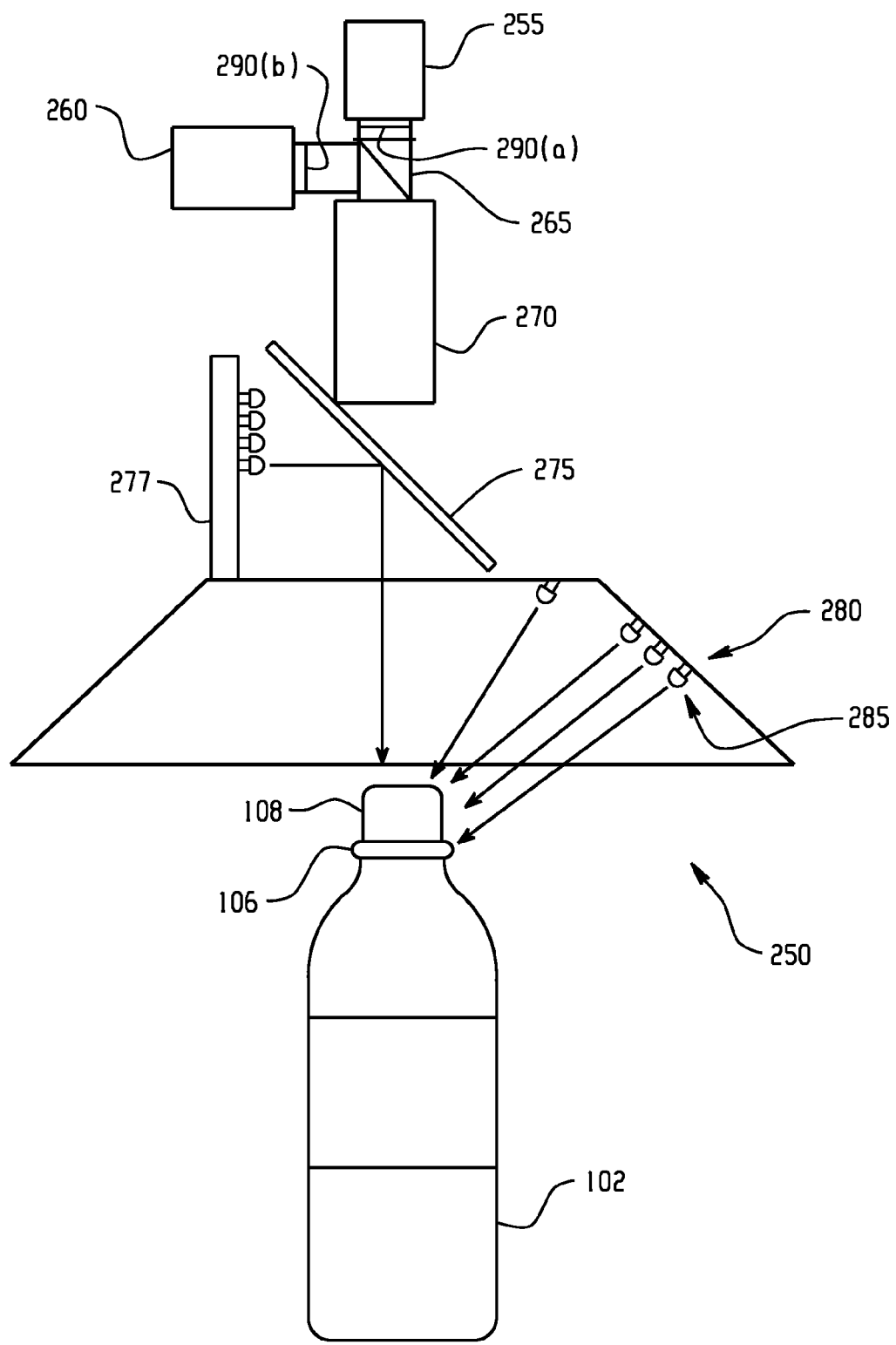

In one form, with continuing reference to FIG. 2(c), an imaging system 120 (of FIG. 1) includes at least camera 255, camera 260 and lensing system 270. The imaging system 120 is configured to capture a first image of a cap fitted to a container by the first camera (e.g. which may be the camera 255 or camera 260 depending on the configuration) and capture a second image of at least a portion of a support ring of the container by a second camera (e.g. which would typically be the other of camera 255 or camera 260 depending on the configuration). It should be appreciated that, with two cameras, images may be obtained simultaneously or non-simultaneously (e.g. sequentially), depending on the application. The processing or computer system 130 (of FIG. 1) is configured to analyze the first image and the second image to determine a removal torque required to remove the cap from the container or a rotational position. The processor or computer system 130 may also determine whether the removal torque is acceptable, perform at least one of sending a reject signal to reject the container and sending a feedback control signal to the capping system, e.g. to adjust torque applied by the capping machine, if the removal torque or rotational position is not acceptable, and repeat analyzing, determining and performing for subsequent caps fitted to containers.

It should be recognized that the beam splitters described herein may take a variety of forms. For example, the beam splitters may be implemented to use different percentages of split depending on the application, conditions, or images.

Figure 3:
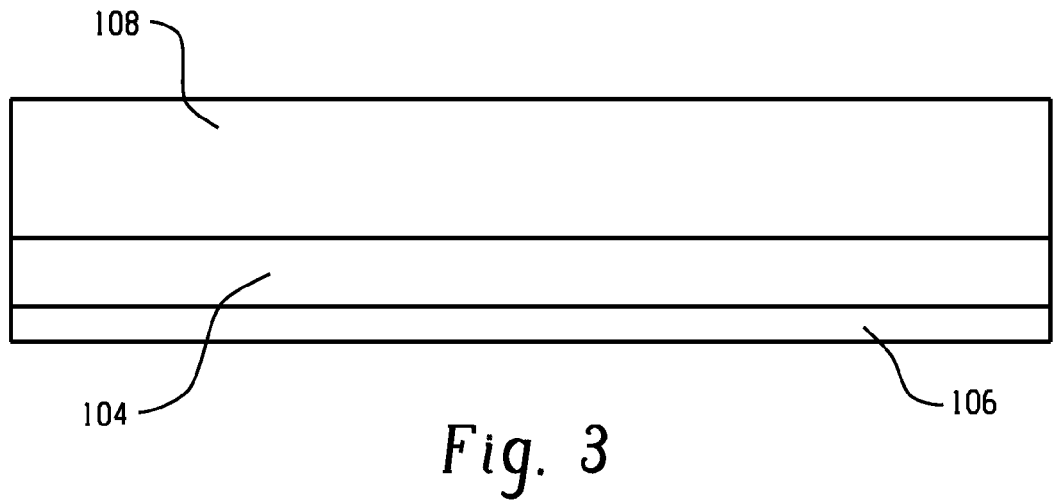
FIG. 3 is a representation of a portion of an image analysis according to the presently described embodiments.

As an option, with reference now to FIG. 3, the presently described embodiments may manipulate the obtained image to unwrap the sidewalls of the cap 108 by circumferential, in-looking lensing (e.g. paracentric lensing mentioned above) which works for certain purposes. As shown, the cap 108, finish portion or neck 104 and support ring 106 are unwrapped for analysis purposes. Other techniques may have different advantages.

Figure 4:
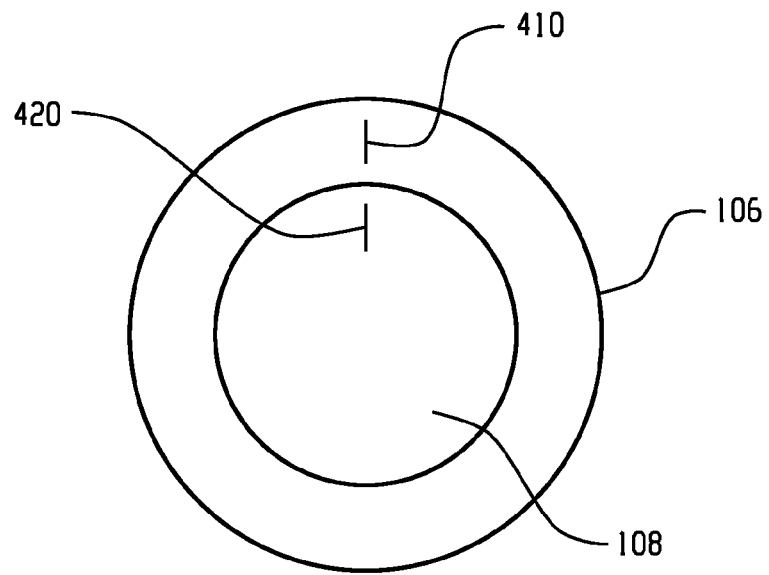
FIG. 4 is a representation of a portion of an image analysis according to the presently described embodiments; and, FIGS. 5(a)-5(c) are flowcharts illustrating example methods according to the presently described embodiments.

With reference to FIG. 4, the presently described embodiments, in at least one form, provide for the neck ring or support ring 106 to have an identifiable orientation feature or fiducial 410 to help assess the rotational orientation of the cap 108. For example, the orientation feature could either be a naturally occurring feature in its normal design aesthetics or specifically molded in for rotational orientation detection (as shown by mark 410) or any combination of the two. Similarly, the cap or closure could have naturally aesthetic features which could be used to detect the bottle, molded features, and/or the thread start features. A special mark or fiducial 420 could be molded in for this purpose and would often be needed. These marks or features could be used alone or in combination (as will be described below in example embodiments) to assess whether the cap is properly fitted to the bottle.

In this regard, for example, it should be appreciated that the marks or fiducials, in at least one form, on the cap can be correlated to the thread pattern on the inside of the cap. In some cases, a dual thread pattern may dictate that more than one fiducial be molded into the cap. Also, the marks or fiducials for the support ring can be correlated to the thread pattern of the bottle.

The presently described embodiments may also provide the neck ring fiducial 410 to be on the top surface and to be one of a 3-D feature molded into the surface to facilitate sufficient contrast for reliable detection by the vision algorithms and could be a visually detectable feature included in the molded bottle finish or preform.

The presently described embodiments may also provide the cap fiducial 420 to be molded into the product such that it creates a robustly detectable condition. There could be a multitude of different geometrical or 3-D ways of incorporating this into the cap. The aesthetics of the cap are important, so it could be skillfully incorporated to allow the vision system to utilize algorithms to detect the rotational location but so it would not be objectionable to the manufacturer of the product or may be completely undetectable by the consumer but very detectable by the vision system. For example, the pattern of a series of flutes around the cap could be very measurable by the algorithm but the consumer would be unaware that it is not uniformly spaced.

The presently described embodiments could be applied to many different types of containers including, but not limited to, plastic bottles, glass bottles, metal cans with a threaded or twist cap or closure removal, or other types of containers having threaded opening facility.

If a neck ring or support ring is not part of the container's design, it is possible to use another visible surface of the container which can incorporate a fiducial mark for the practice of the presently described embodiments.

Also, it should be appreciated that, in at least some circumstances, optimized optics and illumination techniques will improve overall performance and, for example, may facilitate using smaller and less noticeable or less obtrusive fiducials.

The presently described embodiments may also provide a way to visually show on a user interface screen (e.g. of the user interface 150) the rotational position of each. The finish can be shown, for example, at 12:00 position while the cap's final position can be shown relative to the "goal" of 12:00 position.

By incorporating infrared illumination in the presently described embodiments, it is possible to put the fiducial on the inside of the closure to accommodate situations when the fiducial should most desirably not be seen on the outside or by the consumer.

Because of the possible false visual artifacts around the perimeter of a neck ring, including water droplets and visual alterations, the presently described embodiments may also provide that the orientation of the cap (e.g. and/or the location of the cap fiducial) would be algorithmically determined first. This approach will limit the search range required and will thus make the system more robust. More specifically, as will be illustrated below in connection with a description of example methods according to the presently described embodiments, the system may image the cap to determine the location of the mark for the cap. Once the location of the mark for the cap is known, the entire support ring need not be imaged or processed to locate the mark on the support ring. Only a small arc segment of the support ring need be imaged, e.g. an arc segment where the mark is most likely located. This may be determined in any of a variety of ways including based on apriori knowledge. In such a case, for example, an arc segment may be designated to span a specified distance from the located cap mark. There are many advantages to processing only an arc segment (as opposed to the entire support ring) including avoiding image noise (stray marks, water droplets, . . . etc.) that might be created by processing the entire ring. Another advantage is apparent in the dual thread configurations where multiple marks are used on the cap. Because only one mark is needed for purposes of the presently described embodiments, the other marks will not be processed incorrectly if the arc segment approach is correctly used.

Figure 5A:
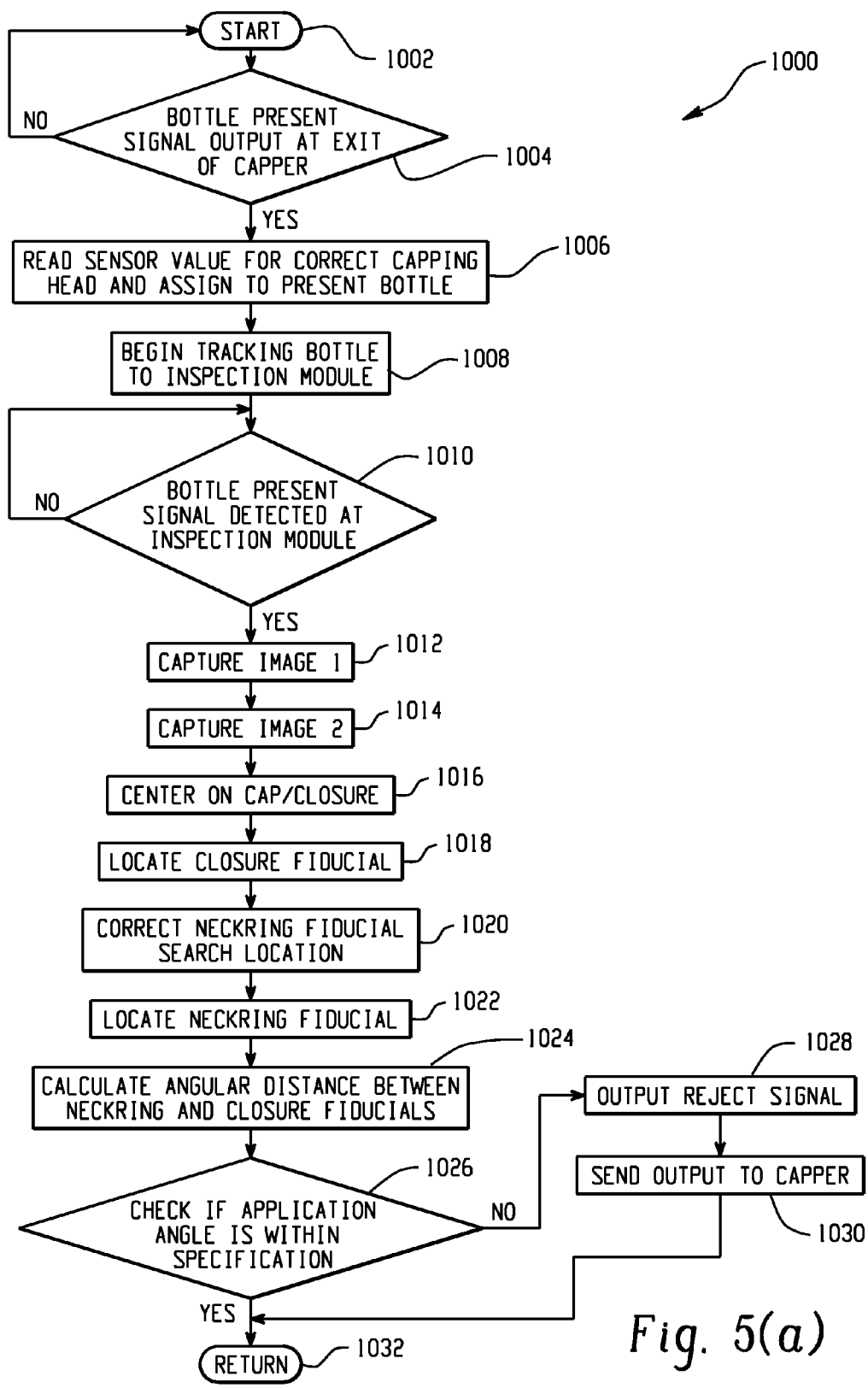
Figure 5B:
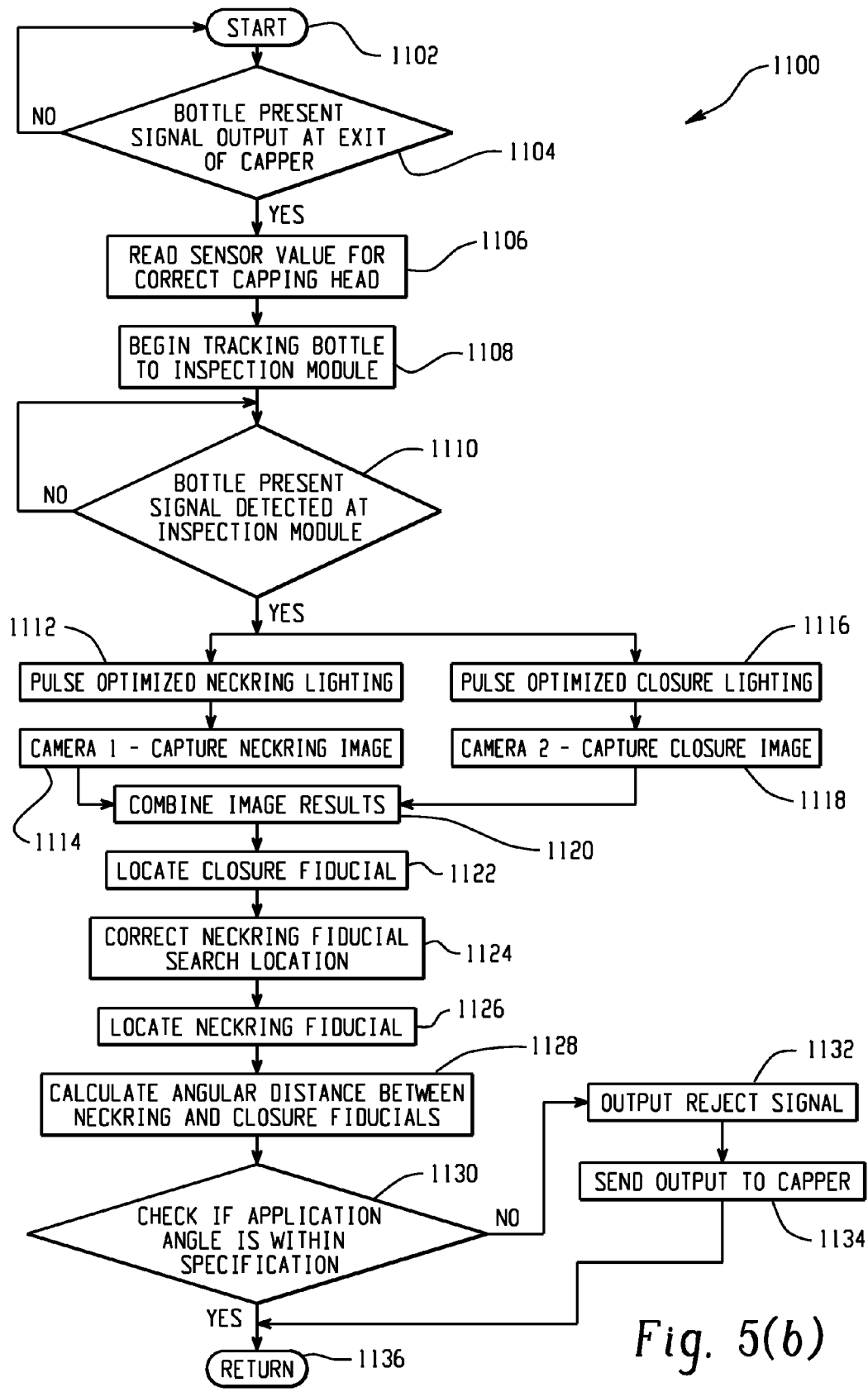

With reference now to FIGS. 5(*a*)-(*c*), various methods according to the presently described embodiments are described. It should be appreciated that the methods according to the presently described embodiments may be implemented using a variety of hardware configurations and/or software techniques. For example, suitable software routines may be maintained and/or executed using suitable hardware such as memory devices and/or the noted processing computers or processors in or associated with the system.

In this regard, generally, a method is initiated by obtaining or capturing images of capped containers. The obtained images are analyzed in a variety of manners to determine an estimate of a removal torque to remove the cap from the bottle or a rotational position of the cap. This can be accomplished in any of a variety of manners, including those described above in connection with FIGS. 2, 3 and 4. Next, optionally, a determination is then made as to whether the estimated removal torque or rotational position is acceptable. This could be accomplished in a variety of manners, including comparing the estimated value with a calculated composite tolerance range to determine if the estimated value falls within an acceptable range.

If the estimated removal torque or rotational position is acceptable, the process is simply repeated for the next capped bottle and, optionally, the information may be used and/or maintained. If the estimated removal torque or rotational position is not acceptable, in some cases, a reject signal is provided to the reject mechanism by the processing system to remove or reject the bottle from the process. Further, in some cases, a feedback control signal may be provided to the capping machine by the processing system.

If, in the process of measuring or determining the removal torque or the rotational position of the cap with the presently described embodiments, other bottle defects are found, they can be correlated back to the particular machine parts that were associated with the subject container. For example, the condition of the neck or support ring may be utilized by the system. In this example, telecentric lenses may be advantageously used to capture images and inspect the neck or support ring.

Also, it should be appreciated that the system may track, compile, store, maintain, feedback, utilize, and/or present to the user all or part of the information determined using the presently described embodiments—not just information or feedback relating to rejections of items. Further, other information such as different views of the cap or bottle may be provided and/or maintained by the system.

The presently described embodiments may also use statistical trending information that can also be useful in the process optimization of each capper head. This could be shown as an SPC graph indication of least one of average, min/max, standard deviation, CPK, CP, torque range, rotational position of the cap etc.

With reference now more specifically to FIG. 5(*a*), the method 1000 is illustrated. This method begins (at 1002). A determination is made as to whether a bottle is present at the exit of the capping machine (at 1004). If not, the system waits. If, however, a bottle is present, a sensor value to determine the correct capping head for the bottle is read and assigned to the bottle (at 1006). The bottle is then tracked to the inspection module (at 1008). A determination is made as to whether the bottle is present at the inspection module (at 1010). If, not, the system waits. If, however, the bottle is present, a first image is captured (at 1012). The first image could be an image of the cap or closure. Also, the first image could be captured in conjunction with a pulse or otherwise intelligent operation of the contemplated engineered lighting system. Next, a second image is captured (at 1014). The second image could be an image of the support ring. Also, the second image could be captured in conjunction with a pulse or otherwise intelligent operation of the contemplated engineered lighting system. It should be appreciated that, in at least one form, the image capturing is accomplished non-simultaneously. Next, the images are analyzed to center on the cap of the first image (at 1016). The cap or closure fiducial is then located (at 1018). A process is then conducted to determine the correct neck ring fiducial search location (at 1020). As noted above, the entire neck or support ring may not need to be analyzed, only an arc segment thereof. The neck ring fiducial is then located (at 1022). The angular distance between the neck ring fiducial and the closure fiducial is then calculated (at 1024). Optionally, then, a determination is then made whether the calculated angle is within specification (at 1026). If not, optionally, a reject signal is provided to the reject mechanism (at 1028). Also, optionally, feedback is provided to the capper machine (at 1030). Next, the technique is repeated for subsequent bottles (at 1032).

With reference now to FIG. 5(*b*), a method 1100 is illustrated. The method 1100 is initiated (at 1102). Next, it is determined whether a bottle is present at the output of the capper machine (at 1104). If not, the system waits. If, however, a bottle is present at the output of the capper machine, a sensor value to determine the correct capping head is read (at 1106). The bottle is then tracked to the inspection module (at 1108). A determination is then made as to whether a bottle is present at the inspection module (at 1110). If not, the system waits. If, however, a bottle is detected at the inspection module, the optimized neck ring lighting is pulsed or otherwise operated in an intelligent and/or engineered manner (at 1112). During the pulse or operation, a first camera captures the neck ring image (at 1114). Simultaneously with the capture of the first image, the optimized closure lighting is pulsed or otherwise operated in an intelligent and/or engineered manner (at 1116). A second camera captures a neck ring image (at 1118). The image results are combined (at 1120). It should be appreciated that the combination of images may be accomplished in a variety of manners that will be apparent to those in the field. However, in one form, through software routines, electronics and other suitable hardware, the images are combined to form a composite image having suitable (e.g. optimized) views of the support ring and cap fiducials or marks. This allows the user to view a single image of both fiducials or marks (e.g. in an optimized view) and provides for convenient storage of a single image for future reference. Another approach to address the multiple images is to capture each image and locate the fiducials independently. The polar locations of each fiducial can be determined and the angular offset measured. The closure fiducial is located (at 1122). A determination is then made as to the correct neck ring fiducial search location (at 1124). As noted above, the entire neck or support ring may not need to be analyzed, only an arc segment thereof. The neck ring fiducial is then located (at 1126). An angular distance between the neck ring fiducial and the closure fiducial is then calculated (at 1128). Optionally, a determination is then made as to whether the calculated angle is within the specification (at 1130). If not, optionally, a reject signal is output to a reject mechanism (at 1132). Also, feedback is optionally provided to the capper machine (at 1134). The process is then repeated for subsequent bottles (at 1136).

Figure 5C:
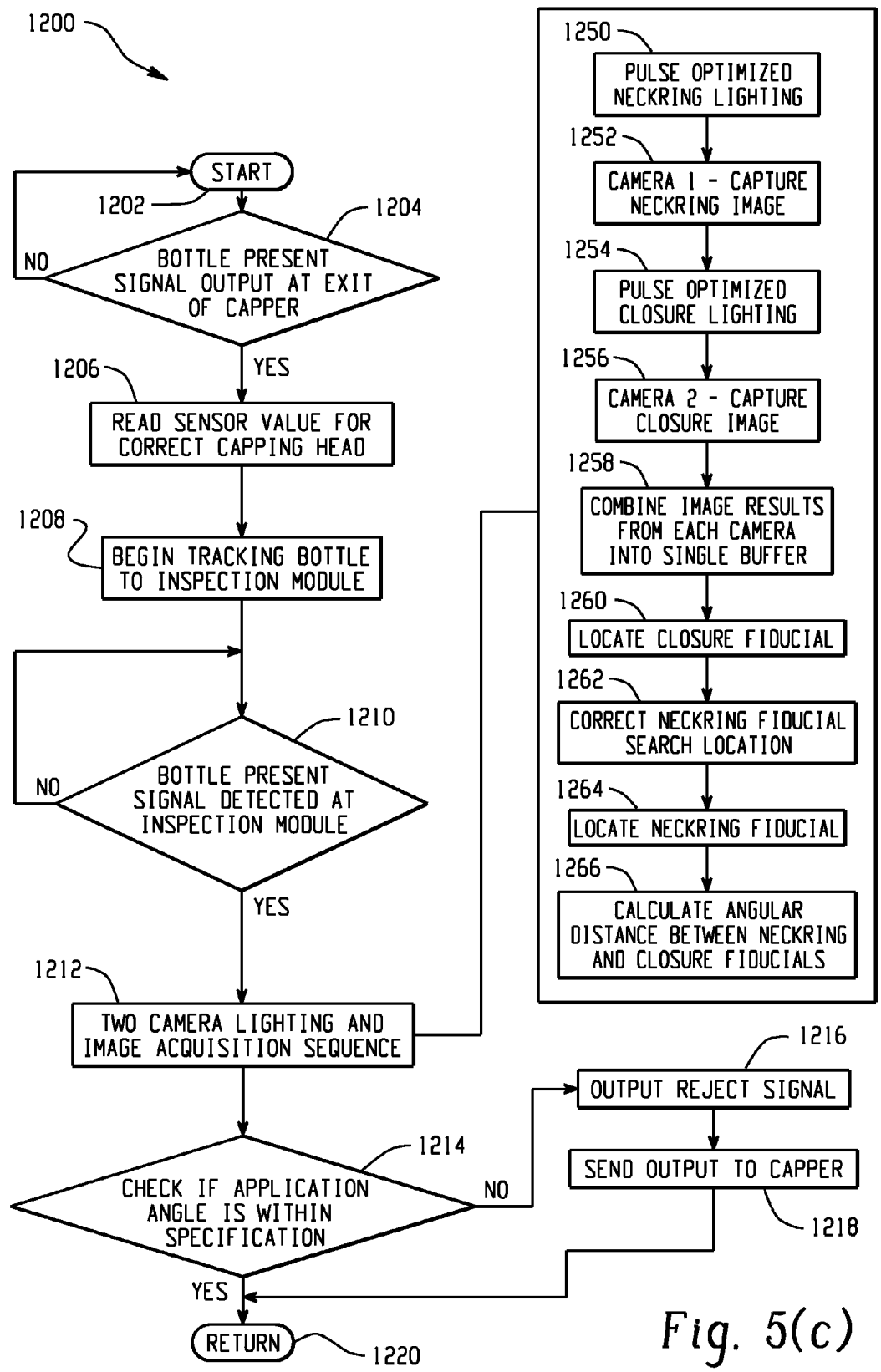

With reference now to FIG. 5(c), another method 1200 is illustrated. The method 1200 is started (at 1202). A determination is first made as to whether a bottle is present at the exit of the capper machine (at 1204). If not, the system waits. If, however, a bottle is present at the exit of the capper machine, a sensor value to determine correct capping head is read (at 1206). Then, the bottle is tracked to the inspection module (at 1208). A determination is then made as to whether the bottle is detected at the inspection module (at 1210). If not, the system waits. If, however, the bottle is detected at the inspection module, a two camera lighting and image acquisition sequence is initiated (at 1210). After the lighting and image acquisition sequence is accomplished, optionally, a determination is made as to whether the calculated angle is within specification (at 1214). If not, optionally, a reject signal is output to the reject mechanism (at 1216). Also, the feedback is optionally output to the capper machine (at 1218). At the end of the process for a particular bottle, the process is repeated for subsequent bottles (at 1220).

With respect to the two camera lighting and image acquisition sequence (at 1210), the optimized neck ring lighting is pulsed (at 1250). During the pulse of the lighting, a first camera captures the neck ring image (at 1252). Next, optimized closure lighting is pulsed (at 1254). During this pulse, a closure image is captured by a second camera (at 1256). The image results from each camera is combined into a single buffer (at 1258). It should be appreciated that the combination of images may be accomplished in a variety of manners that will be apparent to those in the field. However, in one form, through software routines, electronics and other suitable hardware, the images are combined to form a composite image having suitable (e.g. optimized) views of the support ring and cap fiducials or marks. This allows the user to view a single image of both fiducials or marks (e.g. in an optimized view) and provides for convenient storage of a single image for future reference. Another approach to address the multiple images is to capture each image and locate the fiducials independently. The polar locations of each fiducial can be determined and the angular offset measured. The closure fiducial is located (at 1260). Based on this information, a determination is made as to the correct neck ring fiducial search location (at 1262). As noted above, the entire neck or support ring may not need to be analyzed, only an arc segment thereof. Based thereon, the neck ring fiducial is located (at 1264). Then, the angle or distance between the neck ring fiducial and the closure fiducial is calculated (at 1266).

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A method useful in a filling and capping system for analyzing caps fitted to containers having support rings by a capping machine, the caps and support rings having fiducials, marks or orientation patterns consistently oriented with respect to a start of their respective thread elements, the method comprising:
    capturing a first image of a cap fitted to a container;
    capturing a second image of at least a portion of a support ring of the container, wherein the capturing of the first image and the second image occurs non-simultaneously; and,
    analyzing the first image and the second image to determine a removal torque required to remove the cap from the container based on the fiducials, marks or orientation patterns.

2. The method as set forth in claim 1 further comprising:
    determining whether the removal torque is acceptable;
    if the removal torque is not acceptable, performing at least one of sending a reject signal to reject the container and sending a feedback control signal to the capping system; and,
    repeating the capturing, analyzing, determining and performing for subsequent caps fitted to containers.

3. The method as set forth in claim 1 wherein the obtaining the at least two images is accomplished using multiple cameras.

4. The method as set forth in claim 1 wherein the obtaining the at least two images is accomplished using telecentric lensing.

5. The method as set forth in claim 4 wherein the support ring is inspected using the telecentric lens.

6. The method as set forth in claim 1 wherein the analyzing of the at least two images comprises comparing a final rotational position of the cap relative to the container to estimate the removal torque.

7. The method as set forth in claim 4 wherein the rotational position is determined based on positions of fiducials or marks.

8. The method as set forth in claim 2 wherein the feedback control signal facilitates torque correction for multiple capper heads of the capping machine.

9. The method as set forth in claim 1 further comprising using at least one of engineered lighting and filters to obtain images.

10. A method useful in a filling and capping system for analyzing caps fitted to containers having support rings by a capping machine, the caps and support rings having fiducials, marks or orientation patterns consistently oriented with respect to a start of their respective thread elements, the method comprising:
    capturing a first image of a cap fitted to a container using a first camera;

capturing a second image of at least a portion of a support ring of the container using a second camera; and,
analyzing the first image and the second image to determine a removal torque required to remove the cap from the container based on the fiducials, marks or orientation patterns.

11. A method as set forth in claim 10 further comprising:
determining whether the removal torque is acceptable;
if the removal torque is not acceptable, performing at least one of sending a reject signal to reject the container and sending a feedback control signal to the capping system; and,
repeating the capturing, analyzing, determining and performing for subsequent caps fitted to containers.

12. The method as set forth in claim 10 wherein the obtaining the first and second image is accomplished using telecentric lensing.

13. The method as set forth in claim 12 wherein the support ring is inspected using the telecentric lens.

14. The method as set forth in claim 10 wherein the analyzing of the at least two images comprises comparing a final rotational position of the cap relative to the container to estimate the removal torque.

15. The method as set forth in claim 14 wherein the rotational position is determined based on positions of fiducials or marks.

16. The method as set forth in claim 11 wherein the feedback control signal facilitates torque correction for multiple capper heads of the capping machine.

17. The method as set forth in claim 10 further comprising using at least one of engineered lighting and filters to obtain images.

18. A system useful in a filling and capping system for analyzing caps fitted to containers having support rings by a capping machine, the caps and support rings having fiducials, marks or orientation patterns consistently oriented with respect to a start of their respective thread elements, the system comprising:
an imaging system including at least one camera and a lensing system, the imaging system being configured to capture a first image of a cap fitted to a container, capture a second image of at least a portion of a support ring of the container, wherein the capturing of the first image and the second image occurs non-simultaneously; and,
a processing system configured to analyze the first image and the second image to determine a removal torque required to remove the cap from the container based on the fiducials, marks or orientation patterns.

19. The system as set forth in claim 18 wherein the processing system is configured to determine whether the removal torque is acceptable, perform at least one of sending a reject signal to reject the container and sending a feedback control signal to the capping system if the removal torque is not acceptable, and repeat analyzing, determining and performing for subsequent caps fitted to containers.

20. The system as set forth in claim 18 wherein the obtaining the at least two images is accomplished using multiple cameras.

21. The system as set forth in claim 18 wherein the lensing system comprises a telecentric lens system.

22. The system as set forth in claim 18 wherein the processing system is configured to analyze the at least two images by comparing a final rotational position of the cap relative to the container to estimate the removal torque.

23. The system as set forth in claim 22 wherein the rotational position is determined based on positions of fiducials or marks.

24. The system as set forth in claim 19 wherein the feedback control signal facilitates torque correction for multiple capper heads of the capping machine.

25. The system as set forth in claim 18 further comprising a user interface.

26. A system useful in a filling and capping system for analyzing caps fitted to containers having support rings by a capping machine, the caps and support rings having fiducials, marks or orientation patterns consistently oriented with respect to a start of their respective thread elements, the system comprising:
an imaging system including at least a first camera, a second camera and a lensing system, the imaging system being configured to capture a first image of a cap fitted to a container by the first camera, capture a second image of at least a portion of a support ring of the container by a second camera; and,
a processing system configured to analyze the first image and the second image to determine a removal torque required to remove the cap from the container based on the fiducials, marks or orientation patterns.

27. The system as set forth in claim 26 wherein the processing system is configured to determine whether the removal torque is acceptable, perform at least one of sending a reject signal to reject the container and sending a feedback control signal to the capping system if the removal torque is not acceptable, and repeat analyzing, determining and performing for subsequent caps fitted to containers.

28. The system as set forth in claim 26 wherein the lensing system comprises a telecentric lens system.

29. The system as set forth in claim 26 wherein the processing system is configured to analyze the at least two images by comparing a final rotational position of the cap relative to the container to estimate the removal torque.

30. The system as set forth in claim 29 wherein the rotational position is determined based on positions of fiducials or marks.

31. The system as set forth in claim 27 wherein the feedback control signal facilitates correction for multiple capper heads of the capping machine.

32. The system as set forth in claim 26 further comprising a user interface.

33. The method as set forth in claim 1 further comprising analyzing the first image and the second image to determine a rotational position of the cap.

34. The method as set forth in claim 10 further comprising analyzing the first image and the second image to determine a rotational position of the cap.

35. The system as set forth in claim 18 wherein the processing system is further configured to analyze the first image and the second image to determine a rotational position of the cap.

36. The system as set forth in claim 26 wherein the processing system is further configured to analyze the first image and the second image to determine a rotational position of the cap.

37. The method as set forth in claim 1 further comprising optimizing lighting during capturing the first image.

38. The method as set forth in claim 1 further comprising optimizing lighting during capturing the second image.

39. The method as set forth in claim 10 further comprising optimizing lighting during capturing the first image.

40. The method as set forth in claim 10 further comprising optimizing lighting during capturing the second image.

41. The system as set forth in claim 18 wherein the determined removal torque provides a basis for manual correction of the capping machine.

42. The system as set forth in claim 26 wherein the determined removal torque provides a basis for manual correction of the capping machine.

* * * * *